(12) United States Patent
Charlton

(10) Patent No.: US 8,003,333 B2
(45) Date of Patent: Aug. 23, 2011

(54) SERUM BIOMARKERS FOR EARLY DETECTION OF ACUTE CELLULAR REJECTION

(75) Inventor: Michael R. Charlton, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 185 days.

(21) Appl. No.: 12/235,292

(22) Filed: Sep. 22, 2008

(65) Prior Publication Data

US 2009/0088409 A1    Apr. 2, 2009

Related U.S. Application Data

(60) Provisional application No. 60/975,993, filed on Sep. 28, 2007.

(51) Int. Cl.
G01N 33/53 (2006.01)
G01N 33/49 (2006.01)

(52) U.S. Cl. ...... 435/7.1; 435/7.92; 435/7.93; 435/7.94; 435/7.95; 435/366; 435/372

(58) Field of Classification Search .................. None
See application file for complete search history.

(56) References Cited

FOREIGN PATENT DOCUMENTS

WO    WO 2006/099421    *    9/2006

OTHER PUBLICATIONS

Hartmann et al, Nephrol Dial Tranplant 12: 161-166, 1997.*
Walker et al, Transplantation Proceedings 34: 1279-1280, 2002.*
Andrews et al., Blood, Jul. 1983;62(1):124-132.
Belov et al., Analytical Chem. May 15, 2000;72(10):2271-2279.
Berenguer et al., J. Hepatol. May 1998; 28(5):756-763.
Birk et al. Nat. Acad. Sci. Apr. 27, 1999; 96 (9 ):5159-63.
Bjorhall et al., Proteomics Jan. 2005; 5(1):307-317.
Borozdenkova et al., J. Proteome Res. Mar.-Apr. 2004; 3(2): 282-8.
Charlton et al., Liver Transplantation & Surgery Jul. 1999; 5(4:Suppl 1):107-114.
Chen et al., Cancer Research Nov. 15, 2005; 65 (22 ):10394-400.
Chong et al., J. Proteome Res. May 2006; 5(5):1232-1240.
Clarke et al., Ann. Surgery May 2003; 237 (5):660-4; discussion 664-5.
Davey et al., Leukemia Jul. 1988; 2(7):420-426.
Demetris et al., Hepatology Mar. 31, 2000(3):792-799.
Deng et al., Transplantation Nov. 27, 1995; 60(10):1118-1124.
DeSouza et al., Proteomics Jan. 5, 2005(1):270-281.
DeSouza et al., J. Proteome Res. Mar. 2005; 4(2):377-386.
Fang et al., Science Nov. 30, 2001; 294 (5548 ):1942-5.
Gao et al., Science Oct. 4, 1908; 306(5694):271-275.
Gilks et al., Mol. & Cell. Biology Mar. 1993; 13(3):1759-1768.
Granja et al., Hum. Immunology Feb. 2004; 65 (2):124-34.
Griffin et al., Leukemia Research 1984;8(4):521-534.
Gygi et al., Nature Biotechnology Oct. 1999; 17(10):994-999.
Handgretinger et al., Immunology Letters Aug. 1993; 37(2-3):223-228.
Jacobs et al., J. Proteome Research Jul. 4, 2005(4):1073-1085.
Keshamouni et al., J. Proteome Res. May 2006; 5(5):1143-1154.
Kimball et al., Transplantation Mar. 27, 1996; 61(6):909-915.
Koelman et al., Transplant Immunology Mar. 2000; 8(1):57-64.
Lakkis, Nature Medicine Oct. 2002; 8(10):1043-1044.
Marsh et al., Transplantation Oct. 1, 1915; 72(7):1310-1318.
Martin et al., Analytical Chem. Sep. 15, 2000; 72(18):4266-4274.
Murphy et al., J. Immunology Oct. 2002; 169 (7):3717-25.
Nakamura et al., Blood Mar. 1, 1994; 83(5):1442-1443.
O'Riordan et al., J. Am. Soc. Nephrology Dec. 2004; 15 (12 ):3240-8.
Patterson et al., Cell Stress & Chaperones 2005; 10(4):285-295.
Petricoin et al., Lancet 359 Feb. 2002; (9306 ):572-7.
Pratt et al., Nature Medicine Jun. 2002; 8(6):582-587.
Qian et al., J. Proteome Res. Jan. 2005; 4(1):53-62.
Rajendra et al., J. Biol. Chemistry Aug. 4, 1927; 279(35):36440-36444.
Raptis et al., British J.Haematology Sep. 1998; 102 (5):1354-8.
Rosen et al., Am. J. Gastroenterol Sep. 1997; 92(9):1453-1457.
Sarbassov et al., Current Opinion in Cell Biology Dec. 2005; 17(6 ):596-603.
Satoh et al., Transplantation Sep. 27, 1995;60(6):558-562.
Schaub et al., Am. J. Transplantation Apr. 2005; 5(4 Pt 1):729-738.
Schaub et al., J. Am. Soc. Nephrology Jan. 2004; 15(1):219-227.
Schreiber, Science Jan. 18, 1991; 251(4991):283-287.
Simpson et al., Clinics in Laboratory Medicine Sep. 1991; 11(3):733-762.
Sreekumar et al., Liver Transplantation Sep. 2002; 8(9):814-821.
Tanaka et al., Immunity Jun. 2005; 22(6):729-736.
Thomas et al., J. Immunology Dec. 15, 1993;151(12):6840-6852.
Toyoda et al., Clin. Transplantation Dec. 1995; 9(6):472-480.
Van et al., Cell May 31, 1991; 65(5):737-752.
Venkatesh et al., Nat. Acad. Sci. Jun. 15, 2004; 101 (24):8969-74.
Washburn et al., Nature Biotechnology Mar. 2001; (3):242-247.
Wicks et al., Oncogene Dec. 5, 2001; 24(54):8080-8084.
Wiesner et al., 28 ed. 1998. 638-645. Wu et al., Transplant Immunology Sep. 1994; 2(3):199-207.
Zornig et al., Oncogene Apr. 18, 1996; 12(8):1789-1801.

* cited by examiner

*Primary Examiner* — Phuong Huynh
(74) *Attorney, Agent, or Firm* — Quarles & Brady, LLP

(57) ABSTRACT

The present invention provides an improved method of diagnosing a subject having received an organ transplant with Acute Cellular Rejection (ACR). The method comprises obtaining a biological sample from the subject, detecting an amount of at least one protein indicative of ACR in the sample, and comparing the amount of the protein in the sample to a control, wherein a difference between the amount of the protein in the sample relative to the control indicates the subject has or is developing ACR. The difference can be an increase or a decrease. In one version the biological sample comprises a serum sample, and the transplanted organ is selected from a heart, kidney, liver, bone marrow, pancreas, eye, lung or skin. A kit and methods of treating a subject having an organ transplant for ACR and treating an immune suppressed subject are also provided.

1 Claim, 1 Drawing Sheet

SERUM BIOMARKERS FOR EARLY DETECTION OF ACUTE CELLULAR REJECTION

CROSS-REFERENCE TO RELATED APPLICATIONS

This application claims priority from U.S. provisional patent application Ser. No. 60/975,993 filed Sep. 28, 2007 which is incorporated by reference herein.

STATEMENT REGARDING FEDERALLY SPONSORED RESEARCH OR DEVELOPMENT

Not applicable.

FIELD OF THE INVENTION

The invention relates generally to methods of diagnosing and preventing acute cellular rejection in subjects having received an organ transplant.

BACKGROUND

Identifying noninvasive markers for Acute Cellular Rejection (ACR) has important implications for immunosuppressive management of transplant recipients. To date, diagnosing ACR is based on detecting biochemical evidence of graft dysfunction and the presence of suggestive allograft histology, including a lymphocytic infiltrate.[1,2] The presence of a cellular infiltrate and biochemical abnormalities, however, are not specific to ACR. For instance, the Hepatitis C virus (HCV) has similar clinical and histological effects, and distinguishing between the effects of HCV and ACR is difficult, especially because either or both events may occur simultaneously.

Conventional proteomic studies in kidney transplantation have focused on urine analysis. There are three urine proteomic analyses of acute rejection in renal transplant recipients,[14-16] ultimately identifying urinary beta 2-microglobulin and its fragments as potential biomarkers for ACR.[17] A single report, carried out in follow-up to a tissue proteomic analysis, found, using an ELISA method, that the abundance of alpha B-crystallin and tropomyosin are increased in serum during ACR in heart transplant recipients.[18]

As therapeutic agents that inhibit rejection are associated with more severe infectious complications of transplantation, such as recurring HCV,[3-5] it seems likely that allograft injury due to infections and ACR are mechanistically distinct. ACR is characterized by antigen-triggered T-cell activation and the subsequent migration of activated CD4+ and CD8+ T-cells, macrophages and natural killer (NK) cells. As T-cell activation in ACR is characterized by a consistent and distinct motif of gene expression,[6] ACR is likely also associated with the expression of a subset of T-cell dependent immune activation proteins in serum.

SUMMARY OF THE INVENTION

The present invention provides an improved method of diagnosing a subject having received an organ transplant with Acute Cellular Rejection (ACR). In one embodiment the method comprises obtaining a biological sample from the subject, detecting an amount of at least one protein indicative of ACR in the sample, and comparing the amount of the protein in the sample to a control, wherein a difference between the amount of the protein in the sample relative to the control indicates the subject has ACR. The difference can be an increase or a decrease in the amount of the protein, relative to the control. In one embodiment the biological sample comprises a serum sample, and the organ transplanted is selected from the group consisting of heart, kidney, liver, pancreas, eye, lung or skin.

The protein indicative of ACR is selected from the group consisting of A Chain A (human C-reactive protein), serum amyloid A2-beta (human), C-reactive protein precursor, ubiquitin-conjugating enzyme E2; heat shock protein HSP60; nuclear factor of activated T-cells (T cell transcription factor NFAT1); ubiquitin; heat shock protein HSP70; zinc finger protein 135; complement component 1q; nuclear factor of activated T-cells 2 isoform B; FK506 binding protein 10 precursor; HSP-C078; UDP-glucose pyrophosphorylase 2; complement C3; alpha-fibrinogen precursor; sulfated glycoprotein-2; serum amyloid A1; glyceraldehyde 3-phosphate dehydrogenase; complement component 4A; complement component 4B; proapo-A-I protein; retinol binding protein; A Chain A, crystal structure of a serpin:protease complex; leucine-rich alpha-2-glycoprotein; zinc-alpha-2-glycoprotein precursor; RBP4 gene product; myeloid cell surface antigen CD33 precursor; alpha-2-glycoprotein 1 zinc; FK 506 binding protein 10; AMBP protein precursor; human Apolipoprotein C-I; nuclear protein; zn-alpha2-glycoprotein; apolipoprotein B-100; apolipoprotein-H; serine (or cysteine) proteinase inhibitor; ribosomal protein L15; apolipoprotein D; adenylate kinase 7; plasma protease C1 inhibitor precursor (C1 Inh); beta-2-glycoprotein I precursor; insulin-like growth factor binding protein, ribonucleoprotein autoantigen 60 kd subunit, fibrinogen precursor and apolipoprotien A-I precursor (Apo-AI).

In a preferred embodiment, one would evaluate the sample for the amount of at least one protein listed in Table 4. In other embodiments, the amounts of sets of two, three, four, six, eight, ten, twelve, fifteen, twenty or thirty proteins as listed in Tables 5-15 can be detected and used to diagnose and treat a subject having or developing ACR.

Proteins where an increase in the amount of protein in the sample, relative to the control, is indicative of ACR include A Chain A (human C-reactive protein), serum amyloid A2-beta (human), C-reactive protein precursor, ubiquitin-conjugating enzyme E2; heat shock protein HSP60; Nuclear factor of activated T-cells (T cell transcription factor NFAT1); ubiquitin; heat shock protein HSP70; zinc finger protein 135; complement component 1q; nuclear factor of activated T-cells 2; isoform B; FK506 binding protein 10; precursorHSP-C078; UDP-glucose pyrophosphorylase 2; complement C3; alpha-fibrinogen precursor; Sulfated glycoprotein-2; serum amyloid A1; glyceraldehyde 3-phosphate dehydrogenase; complement component 4A; complement component 4B; proapo-A-I protein; retinol binding protein; A Chain A, crystal structure of a serpin: protease complex; leucine-rich alpha-2-glycoprotein; zinc-alpha-2-glycoprotein precursor; RBP4 gene product; myeloid cell surface antigen CD33 precursor; alpha-2-glycoprotein 1 zinc and AMBP protein precursor.

Proteins where a decrease in the amount of protein in the sample, relative to the control, is indicative of ACR include human apolipoprotein C-I; nuclear protein; zn-alpha2-glycoprotein; apolipoprotein B-100; apolipoprotein-H; serine (or cysteine) proteinase inhibitor; FK binding protein 10; ribosomal protein L15; apolipoprotein D; adenylate kinase 7; plasma protease C1 inhibitor precursor (C1 Inh); beta-2-glycoprotein I precursor; insulin-like growth factor binding protein, ribonucleoprotein autoantigen 60 kd subunit, fibrinogen precursor and apolipoprotien A-I precursor (Apo-AI).

In an alternative embodiment, the method comprises obtaining a biological sample from the subject, detecting an amount of at least two proteins selected from the two-protein sets listed in Table 5 in the sample, and comparing the amount of the proteins in the sample to a control, wherein a difference between the amount of the proteins in the sample relative to the control indicates the subject has ACR. The difference can be an increase or a decrease in the amount of the proteins, relative to the control.

In an alternative embodiment, the method comprises obtaining a biological sample from the subject, detecting an amount of at least three proteins selected from the three-protein sets listed in Table 6 in the sample, and comparing the amount of the proteins in the sample to a control, wherein a difference between the amount of the proteins in the sample relative to the control indicates the subject has ACR. The difference can be an increase or a decrease in the amount of the proteins, relative to the control.

In another alternative embodiment, the method comprises obtaining a biological sample from the subject, detecting an amount of at least four proteins selected from the four-protein sets listed in Table 7 in the sample, and comparing the amount of the proteins in the sample to a control, wherein a difference between the amount of the proteins in the sample relative to the control indicates the subject has ACR. The difference can be an increase or a decrease in the amount of the proteins, relative to the control.

In yet another alternative embodiment of the present invention, a kit for diagnosing a subject having an organ transplant with ACR is provided. The kit comprises a means of detecting a change of at least one protein indicative of ACR, relative to a control, and instructions for use. The proteins wherein a change, relative to the control, indicates that the subject has ACR are selected from Tables 1 and 2. In a preferred embodiment, the kit comprises at least two antibodies specific for at least two proteins selected from Tables 1 and 2.

In another embodiment of the preset invention, a method of treating a subject having received an organ transplant, wherein the subject is developing ACR, is provided. The method comprises obtaining a biological sample from the subject, detecting an amount of at least one protein indicative of ACR in the sample, comparing the amount of the protein in the sample to a control, wherein a difference between the amount of the protein in the sample relative to the control indicates the subject is developing ACR, and treating the subject for ACR.

In another embodiment of the present invention, a method of evaluating a subject for immune suppression is provided. The method comprises obtaining a biological sample from the subject, detecting an amount of at least one protein indicative of immune suppression in the sample, comparing the amount of the protein in the sample to a control, wherein a difference between the amount of the protein in the sample relative to the control indicates the subject has or is developing immune suppression, and treating the subject for immune suppression.

DETAILED DESCRIPTION OF THE INVENTION

In General

Figure 1:
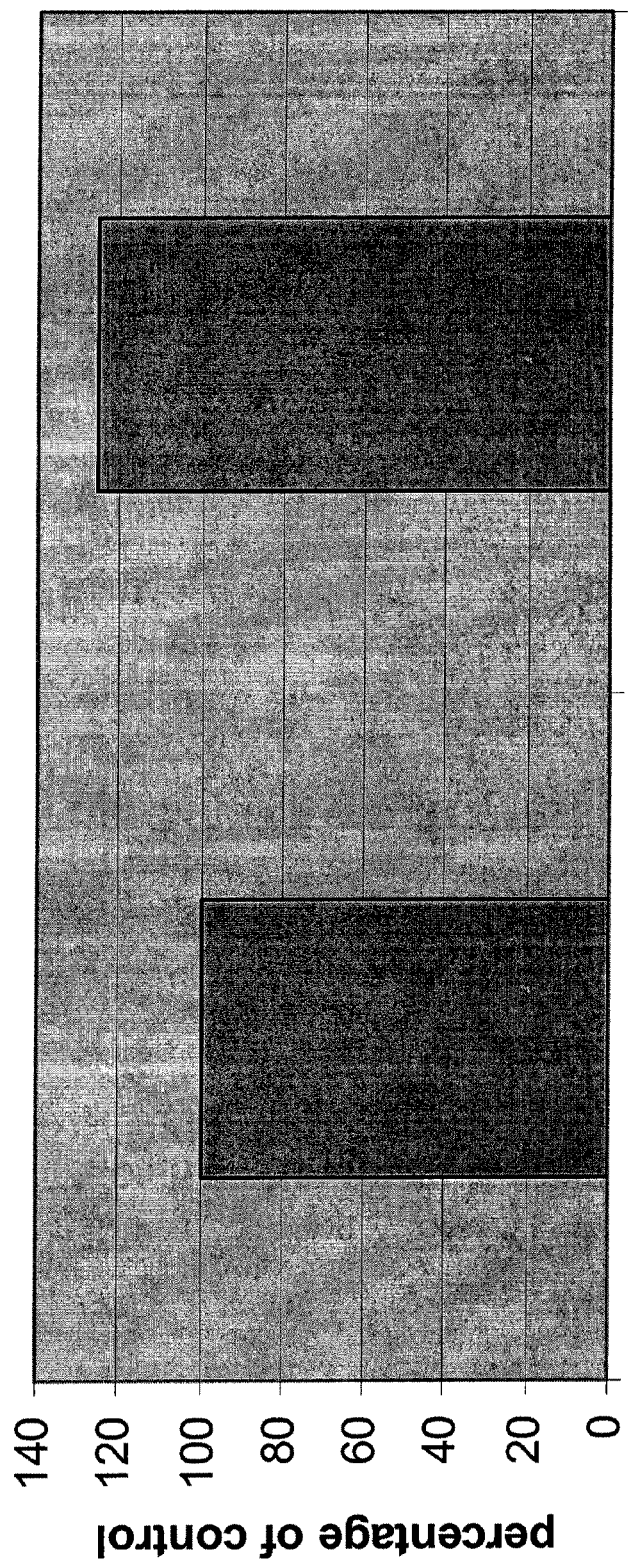
FIG. 1 illustrates detecting a change in the amount of complement C3 in a sample as compared to a control.

An improved method of diagnosing a subject having an organ transplant with Acute Cellular Rejection (ACR) is provided. The method comprises obtaining a biological sample from the subject, detecting an amount of at least one protein indicative of ACR in the sample, and comparing the amount of the protein in the sample to a control, wherein a difference between the amount of the protein in the sample relative to the control indicates the subject has ACR. The difference can be an increase or a decrease. In one version the biological sample comprises a serum sample, and the transplanted organ is selected from a heart, kidney, liver, pancreas, eye, lung or skin.

1. Proteins Indicative of ACR/Immune Suppression

By "proteins indicative of ACR" and "proteins indicative of immune suppression," we mean the proteins listed in Tables 1 and 2. Specifically, we means at least one protein selected from the group consisting of A Chain A (human C-reactive protein), serum amyloid A2-beta (human), C-reactive protein precursor, ubiquitin-conjugating enzyme E2; heat shock protein HSP60; nuclear factor of activated T-cells (T cell transcription factor NFAT1); ubiquitin; heat shock protein HSP70; zinc finger protein 135; complement component 1q; nuclear factor of activated T-cells 2 isoform B; FK506 binding protein 10 precursor; HSP-C078; UDP-glucose pyrophosphorylase 2; complement C3; alpha-fibrinogen precursor; sulfated glycoprotein-2; serum amyloid A1; glyceraldehyde 3-phosphate dehydrogenase; complement component 4A; complement component 4B; proapo-A-I protein; retinol binding protein; A Chain A, crystal structure of a serpin:protease complex; leucine-rich alpha-2-glycoprotein; zinc-alpha-2-glycoprotein precursor; RBP4 gene product; myeloid cell surface antigen CD33 precursor; alpha-2-glycoprotein 1 zinc; FK 506 binding protein 10; AMBP protein precursor; human Apolipoprotein C-I; nuclear protein; zn-alpha2-glycoprotein; apolipoprotein B-100; apolipoprotein-H; serine (or cysteine) proteinase inhibitor; ribosomal protein 15; apolipoprotein D; adenylate kinase 7; plasma protease C1 inhibitor precursor (C1 Inh); beta-2-glycoprotein I precursor; insulin-like growth factor binding protein, ribonucleoprotein autoantigen 60 kd subunit, fibrinogen precursor and apolipoprotien A-I precursor (Apo-AI).

The amounts of any combinations of these proteins may be detected according to the present invention and compared to a control. In one version, a difference in the amount of only one protein can indicate that the subject has or is developing ACR and/or immune suppression. However, in alternate versions, changes in the amounts of any combination of two, three, four, six, eight, ten, twelve, fifteen, twenty, thirty or more proteins can indicate that the subject has or is developing ACR and/or immune suppression.

By "immune suppression" we mean any act that reduces the activation or efficacy of the immune system. Some portions of the immune system itself have immuno-suppressive effects on other parts of the immune system, and immunosuppression may occur as an adverse reaction to treatment of other conditions. Deliberately induced immunosuppression is generally done to prevent the body from rejecting an organ transplant, treating graft-versus-host disease after a bone marrow transplant, or for the treatment of auto-immune diseases such as rheumatoid arthritis or Crohn's disease. This is typically done using drugs, but may involve surgery (splenectomy), plasmapharesis, or radiation. A person who is undergoing immunosuppression, or whose immune system is weak for other reasons (for example, chemotherapy and HIV patients) are said to be immunocompromised.

The difference may be an increase or a decrease. By "increase," we mean the proteins and values listed in Table 1. By "decrease," we mean the proteins and values listed in Table 2. In short, any increase/decrease that is at least 50% relative to the control indicates the subject has or is developing ACR and/or immune suppression.

For ACR, "control" means the protein amounts in a biological sample from an immunosuppressed subject having an organ transplant that does not have and is not developing ACR. For immune suppression, "control" means the protein amounts in a biological sample from a non-immune suppressed subject. In an alternate embodiment of the invention, "control" means healthy, non-transplant patients.

By "transplant" we mean any whole or partial transplant, including without limitation, heart, liver, bone marrow, kidney, pancreas, eye, lung and/or skin transplants. This invention may also apply to subjects receiving multiple, partial or whole transplants.

By "biological sample" we mean a specimen or culture obtained from any source. Biological samples can be obtained from animals (including humans) and may encompass fluids, solids, tissues, and gases. Biological samples may be provided by obtaining a blood sample, biopsy specimen, tissue explant, organ culture, biological fluid or any other tissue or cell preparation from a subject or a biological source. The subject or biological source may be a human or non-human animal. In certain preferred embodiments of the invention, the subject or biological source may be suspected of having or being at risk for having ACR, and in certain other preferred embodiments of the invention the subject or biological source may be known to be free of a risk or presence of such disease.

In certain preferred embodiments the biological sample comprises a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include whole blood, serum, plasma, urine, synovial fluid, cranial or spinal fluid, saliva, tissue infiltrate, cervical or vaginal exudate, tissue infiltrate, pleural effusions, bronchioalveolar lavage fluid, gastric lavage fluid, small or large bowel contents, fecal preparations, serosal fluids, mucosal secretions of the secretory tissues and organs, ascites fluids such as those associated with non-solid tumors, fluids of the pleural, pericardial, peritoneal, abdominal and other body cavities, and the like.

Preferably the sample is a blood sample and especially a serum sample. In certain other embodiments the biological sample is plasma.

2. Detecting Protein Levels

By "detecting," we mean any method known to the art for measuring the amount of protein in the sample. For instance, there are a variety of assay formats known to those of ordinary skill in the art for using an antibody to detect a protein in a sample, including but not limited to enzyme linked immunosorbent assay (ELISA), radioimmunoassay (RIA), immunofluorimetry, immunoprecipitation, equilibrium dialysis, immunodiffusion, immunoblotting, mass spectrometry and other techniques. See, e.g., Harlow and Lane, Antibodies: A Laboratory Manual, Cold Spring Harbor Laboratory, 1988; Weir, D. M., Handbook of Experimental Immunology, 1986, Blackwell Scientific, Boston. For example, the assay may be performed in a Western blot format as described in Example 4, wherein a protein preparation from the biological sample is submitted to gel electrophoresis, transferred to a suitable membrane and allowed to react with the antibody.

As used herein, "subject" means mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex. Preferably the subject is human. Most preferably, the subject is a human having received an organ transplant or an autoimmune disease.

3. Kits

Another aspect of the invention relates to a kit comprising a means of detecting a change in at least one protein indicative of ACR according to the present invention and instructional material. Preferably the kit comprises antibodies specific for at least two proteins listed in Tables 1 and 2. Most preferably, the kit comprises four, five or six antibodies. In an alternative embodiment, the kit comprises a selection of standard amounts of proteins from Tables 1 and 2 for use as controls for such methods of detecting as mass spectrometry.

Instructional material includes a publication, a recording, a diagram, or any other medium of expression which is used to communicate the usefulness of the invention for one of the purposes set forth herein in a human or other mammalian subject. The instructional material of the kit can, for example, be affixed to a container which contains the present invention or be shipped together with a container which contains the invention. Alternatively, the instructional material can be shipped separately from the container with the intention that the instructional material and the means of detecting be used cooperatively by the recipient.

4. Preventing Subjects from Developing ACR

Another aspect of the invention relates a method of treating a subject having received an organ transplant from developing ACR. In a preferred embodiment, the method comprises obtaining a biological sample from the subject, detecting an amount of at least one protein indicative of ACR in the sample, comparing the amount of the protein in the sample to a control, wherein a difference between the amount of the protein in the sample relative to the control indicates the subject is developing ACR, and treating the subject for ACR.

By "treating" we mean identifying a subject exhibiting indications of developing ACR and acting so as to appropriately stop the development of ACR. Specifically, we mean administering to the subject therapeutically effective amounts of pharmaceutical compositions that treat ACR. In one embodiment, we mean adjusting the subject's immunosuppressant dosages so as to treat ACR.

By "developing" we mean a change of at least 50% relative to the control in the amount of any single protein from Tables 1 and 2 or any combination thereof in the biological sample obtained from the subject. A change of at least 50% relative to the control indicates the subject has or is developing ACR, as described in Examples 1 and 2 below.

It is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

2) in subjects in the ACR group when compared to the control group. A change of at least 50% relative to the control group was considered significant.

The thirty-one proteins that significantly increased in expression in the ACR group (Table 1) include A Chain A (human C-reactive protein), serum amyloid A2-beta (human), C-reactive protein precursor, T cell transcription factor NFAT1 and Zinc finger protein (transcription factors), heat shock protein 70 and heat shock protein 60 (stress response/chaperone), ubiquitin-conjugating enzyme E2 and ubiquitin (protein degradation), alpha-2-glycoprotein (lipid metabolism), complement components 1q, 4A and 4B (complement activation and immune function), HSPCO78, leucine rich alpha-2-glycoprotein amyloid cell surface antigen CD33 (cell adhesion) and UDP-glucose pyrophosphorylase 2 and glyceraldehyde 3-phosphate dehydrogenase (glucose metabolism).

TABLE 1

| Protein Name | Function | Fold Change |
| --- | --- | --- |
| Ubiquitin-conjugating enzyme E2 | Protein metabolism | 6.28 ± 0.35 |
| Heat shock protein HSP60 | Chaperone | 5.83 ± 0.27 |
| Nuclear factor of activated T-cells (T cell transcription factor NFAT1) | Transcription factor | 4.87 ± 0.26 |
| Ubiquitin | Protein metabolism | 4.19 ± 0.34 |
| Heat shock protein HSP70 | Chaperone | 3.42 ± 0.12 |
| Zinc finger protein 135 | Transcription factor | 2.88 ± 0.18 |
| A Chain A, Human C-Reactive Protein | Immunity and defense | 2.79 ± 1.89 |
| Complement component 1q | Immunity and defense | 2.54 ± 0.23 |
| Nuclear factor of activated T-cells 2 isoform B | Transcription factor | 2.51 ± 0.16 |
| serum amyloid A2-beta - human | Immunity and defense | 2.49 ± 1.34 |
| FK506 binding protein 10 precursor | Immunity and defense | 2.35 ± 0.11 |
| HSP-C078 | Cell adhesion-mediated signaling | 2.21 ± 0.23 |
| C-reactive protein precursor | Immunity and defense | 2.09 ± 2.04 |
| UDP-glucose pyrophosphorylase 2 | Glucose metabolism | 2.17 ± 0.22 |
| Complement C3 | Complement-mediated immunity | 2.04 ± 0.48 |
| Alpha-fibrinogen precursor | Immunity and defense & Blood clotting | 2.04 ± 0.48 |
| Sulfated glycoprotein-2 | Apoptosis | 2.00 ± 0.32 |
| Serum amyloid A1 | Immunity and defense | 1.99 ± 0.21 |
| Glyceraldehyde 3-phosphate dehydrogenase | Glucose metabolism | 1.94 ± 0.14 |
| Complement component 4A | Immunity and defense | 1.90 ± 0.32 |
| Complement component 4B | Immunity and defense | 1.87 ± 0.32 |
| Proapo-A-I protein | Lipid, fatty acid and steroid metabolism | 1.85 ± 0.11 |
| Retinol Binding Protein | Vitamin/cofactor transport | 1.72 ± 0.26 |
| A Chain A, Crystal Structure Of A Serpin:protease Complex | Protein metabolism and modification | 1.69 ± 0.11 |
| Leucine-rich alpha-2-glycoprotein | Cell adhesion | 1.55 ± 0.21 |
| Zinc-alpha-2-glycoprotein precursor | Lipid, fatty acid and steroid metabolism | 1.55 ± 0.21 |
| RBP4 gene product | Transfer/carrier protein | 1.52 ± 0.26 |
| Myeloid cell surface antigen CD33 precursor | Cell adhesion-mediated signaling; Cell adhesion | 1.51 ± 0.05 |
| Alpha-2-glycoprotein 1, zinc | Lipid, fatty acid and steroid metabolism | 1.51 ± 0.05 |
| FK506 binding protein 10 | Immunity and defense | 1.48 ± 0.07 |
| AMBP protein precursor | Protein metabolism and modification & Proteolysis | 1.45 ± 0.36 |

EXAMPLES

In General

Proteins Differentially Expressed in Serum from Subjects with ACR. Proteins involved with a wide variety of biological functions were found to be differentially abundant between study groups. Out of a total of 2801 proteins analyzed across all serum samples, forty-six proteins were found to be significantly differentially abundant in the sera of all patients with ACR. Of these forty-six proteins, thirty-one were up-regulated (Table 1), and fifteen were down-regulated (Table ACR was also characterized by significantly lower expression of fifteen proteins. These proteins include fibrinogen precursor, apolipoprotein A-I precursor (Apo-AI), apolipoprotein-D, apolipoprotein B-100, apolipoprotein C-I and zinc-alpha-2-glycoprotein (lipid metabolism), insulin-like growth factor binding protein (growth factor), beta-2-glycoprotein I, alpha-fibrinogen (immune function), ribosomal protein L15 (protein synthesis) and adenylate kinase 7 (signal transduction) and the results are shown in Table 2. The functional class of differentially abundant proteins was protein synthesis/degradation (20%), transcription factors (7%), immune function (17%), stress response (5%), glucose metabolism (5%), fatty acid/lipid metabolism (17%), cell signaling (10%), and apoptosis (3%). The largest differential expression between the ACR and control groups (+6.28-fold)

was observed for the ubiquitin-conjugating enzyme E2 a mediator of protein degradation.

TABLE 2

| Protein Name | Function | Fold Change |
| --- | --- | --- |
| Human Apolipoprotein C-I | Lipid Metabolism | 0.80 ± 0.02 |
| Nuclear protein | Nucleic acid metabolism & Pre-mRNA processing | 0.72 ± 0.11 |
| Zn-alpha2-glycoprotein | Lipid, fatty acid and steroid metabolism | 0.63 ± 0.12 |
| Fibrinogen precursor | Coagulation/inflammation | 0.48 ± 0.94 |
| Apolipoprotein A-I precursor (Apo-AI) | Lipid Metabolism | 0.48 ± 0.63 |
| Apolipoprotein B-100 | Lipid Metabolism | 0.46 ± 0.09 |
| Apolipoprotein-H | Immunity and defense | 0.46 ± 0.03 |
| Serine (or cysteine) proteinase inhibitor | Protein metabolism | 0.36 ± 0.21 |
| Ribosomal protein L15 | Protein metabolism | 0.31 ± 0.02 |
| Apolipoprotein D | Lipid, fatty acid and steroid metabolism | 0.26 ± 0.32 |
| Adenylate kinase 7 | Signal transduction | 0.26 ± 0.02 |
| Plasma protease C1 inhibitor precursor (C1 Inh) | Protein metabolism | 0.23 ± 0.11 |
| Beta-2-glycoprotein I precursor | Immunity and defense | 0.21 ± 0.04 |
| Insulin-like growth factor binding protein | Growth factor | 0.17 ± 0.06 |
| Ribonucleoprotein autoantigen 60 kd subunit | Protein metabolism | 0.12 ± 0.04 |

The proteins found to be differentially abundant in ACR are diverse in known functions, including transcription factors, stress response, protein degradation, lipid metabolism, complement activation and immune function, cell adhesion, growth factors and signal transduction. Identifying a distinct serum proteomic signature for ACR, which includes proteins not previously associated with ACR, raises the possibility of new diagnostic and therapeutic approaches to the management of immunosuppression in LT and, perhaps, other organ transplant recipients.

A single mass spectrum is limited to a dynamic range of $<10^{4-5}$. Serum protein, however, has a dynamic range of $>10^{10}$, ranging from albumin at >4.5 g/dL to the cytokines at 1-10 pg/mL. As LC-MS analysis has absolute detection limits in the attomole-zeptomole range[19,20] the sensitivity of serum proteomic analysis is limited not by the lower limits of detection of the instrument but by the presence of the high abundance proteins. To circumvent this limitation, a recently described high abundance protein depletion method[7] was used. Albumin, IgG, IgA, anti-trypsin, transferrin, and haptoglobin were selectively removed from the serum samples using high-performance liquid chromatography that removed approximately 94% of total serum protein. All of the differentially abundant proteins in our analysis were thus present only in small amounts in serum.

In contrast to previous proteomic analyses of serum, the iTRAQ peptide label was employed. iTRAQ is a multiplexed set of four isobaric reagents which are amine specific, eliminating the dependence on relatively non-abundant cysteine containing peptides intrinsic to ICAT-based methods,[21] and yield labeled peptides which are identical in mass and hence also identical in single MS mode, but which produce strong, diagnostic, low-mass MS/MS signature ions.[22, 23] This difference in labeling strategy allows the tagging of most tryptic peptides, simplifying analysis and increasing analytical precision.[13] While there are still many ultra-low abundance proteins that were differentially quantified, the protein depletion/iTRAQ approach described herein yielded considerable novel information.

For instance, the diverse function of the proteins found to be differentially abundant in ACR suggests a complex basis for the serum protein signature. The overall pattern of differentially abundant proteins suggests increased immune activation in ACR when compared to the controls, who had HCV infection in the absence of ACR. Reported peripheral blood markers of immune activation include IL-2,[24, 25] soluble L-2R,[24, 26] IL-6,[26, 27] IL-7,[28] IL-8,[27] IFN-gamma,[24] soluble ICAM-1,[29] and soluble major histocompatibility complex antigens.[30] None of these were identified as differentially abundant. This does not imply that levels of these immune activation markers are not elevated in ACR, but rather that their levels were not measurably different from those seen in the serum of our control group—liver transplant recipients with HCV infection.

In contrast, the mediators of immune activation found to be differentially overabundant in the ACR group were T-cell transcription factor NFAT-1, heat shock proteins (HSP) 60 and 70, complement components 1q, 3, 4A and 4B and CD33. The differential abundance of these proteins merits individual consideration.

NFATs 1, 2 and 4 are induced by calcineurin and transactivate cytokine genes that regulate proliferative responses of T cells.[31] The major immunosuppressive action of calcineurin inhibitors is prevention of nuclear translocation NFAT.[32] The relative increased abundance of NFAT-1 in the ACR group may have conferred increased susceptibility to ACR and resistance to calcineurin inhibition.

HSPs are a ubiquitously expressed and highly conserved family of molecules. Immune reactivity to HSPs, which are elevated in ischemia-reperfusion injury, has been implicated in the pathogenesis of ACR. Anti-HSP immune reactivity is thought to be important in transplant rejection responses. Of particular interest is that proliferation to Hsp60 and Hsp70, both relatively overabundant in ACR in the analysis described herein, has been significantly associated with rejection.[33, 34] C-reactive protein precursor and C-reactive protein, which have been reported to be overexpressed in other inflammatory conditions but not previously specifically associated with ACR, are determined herein to be consistently overexpressed in subjects having or developing ACR.

Further, HSP 60 and 70 gene expression has been reported to be increased in cardiac allografts during ACR.[18] Complement components 1q, 3, 4A and 4B were all over-expressed in ACR. The complement system is known to participate in antigen-specific immune stimulation as well as non-specific inflammation. T-cells, B-cells and antigen-presenting cells (APCs) express complement receptors that respond to stimulation by split complement products, including C4a and C4b. T-cell and APC cell surfaces also bear several complement control proteins that recognize covalently bound fragments of C4 that are capable of signal transduction with subsequent T-cell and APC activation in ACR.[35-37]

CD33, another T-cell activating protein, was also over-expressed in ACR in our experiments. CD33 is a 67-kd glycoprotein that, although found predominantly on myeloid cells,[38, 39] has also been reported on dendritic cells, natural killer (NK) cells, and in vitro-expanded T cells.[40-43] Although there are no reports on the role of CD33+ cells in ACR in liver transplantation, following bone marrow stem cell transplantation allo-responses against hemopoietic progenitor cells (HPC) bearing CD33, cause graft rejection.[44] Whether the overexpression of CD33 contributed to alloimmunity or was a marker of T-cell induction in subjects with ACR cannot be ascertained.

Ubiquitin was also greatly over-expressed in the ACR group. Ubiquitin is a highly conserved polypeptide of 76 amino acids (~9 kDa) that has the unique ability to form multimers once attached to a target substrate. Ubiquitin modification is important in regulating signal transduction and gene expression of a variety of proteins, including TGF[beta]/SMAD, STAT, Jun, and p53.[45-48] The impact of lower circulating levels of ubiquitin is hard to predict as the actions of ubiquitin are so diverse and occur intracellularly. No known reports exist regarding a differential abundance of circulating ubiquitin levels in ACR, nor a known role for ubiquitin in ACR. The zinc finger transcription factor Kruppel-like factor 4 (KLF4), a potent negative regulator of cell proliferation, however, is inhibited by extracellular ubiquitin.[49] Taken together, the relative overabundance of these proteins in ACR may provide a novel index of immune activation.

Interpreting the relative overabundance of zinc finger protein 135 is similarly difficult. Zinc fingers are transcriptional regulatory proteins containing tandemly repeated zinc finger domains. Zinc fingers have diverse effects, including stimulation of interleukin-2 independent growth of T-cells.[50-52] However, the impact of zinc finger protein 135 in alloimmunity and inflammation is not known.

FKBP65 (65-kDa FK506-binding protein), which, along with its precursor protein was relatively overabundant in ACR, belongs to the highly conserved immunophilin family of intracellular proteins.[53] FKBP65, which is not expressed in liver, assists in cis-trans isomerization of X-proline bonds in newly synthesized proteins and is up-regulated in response to tissue injury.[54] Up-regulation of FKBP65 may have been on the basis of increased non-hepatic tissue injury in ACR.

Several proteins that were relatively under-abundant are also of particular interest: IGFBP-1, alpha-fibrinogen, and adenylate kinase 7. Hepatic IGFBP-1 synthesis is under the regulation of mTOR, an important regulator of T-cell signaling cascades and T-cell responsiveness.[55, 56] Lower IGFBP-1 levels suggests lower mTOR levels. If lower serum levels of IGFBP-1 are indicative of lower intracellular mTOR levels, lower serum IGFBP-1 levels may be a surrogate of relatively greater baseline immune activation. Fibrinogen precursor, a procoagulant, was also relatively under-expressed in subjects having or developing ACR, perhaps reflecting impaired hepatic synthesis or increased consumption.

It would be reasonable to consider whether the differential abundance of proteins observed herein was simply due to inflammation, rather than incipient or sub-clinical ACR. This possibility was considered prior to conducting the study and controls, age and gender matched subjects with HCV infection also undergoing protocol liver day seven post-LT liver biopsies that were matched for biochemical profiles and degree of necroinflammation were chosen accordingly. For instance, both the ACR and control groups had HCV infection. Levels of immunosuppression were also similar between study groups by design (as measured by tacrolimus troughs, corticosteroid and mycophenolate mofetil dosing).

Although parameters of immunosuppression were similar between groups it is possible, indeed likely, that the physiological levels of immunosuppression were, in fact, different between groups as evidenced by the subsequent development of ACR soon after the biopsies were obtained. This suggests that indices of immune activation may be more predictive of ACR than twelve hour tacrolimnus troughs, which do not take into account differences in baseline innate or adaptive immunity between subjects.

The following examples set forth preferred aspects of the present invention. It is to be understood, however, that these examples are provided by way of illustration and nothing therein should be taken as a limitation upon the overall scope of the invention.

Materials and Methods

Subjects. Two groups of subjects were studied:

1) ACR group: This group comprised eight liver transplant (LT) recipients with HCV infection who had Banff criteria for acute cellular rejection (ACR) on protocol day 21 liver biopsies. It should be noted that the presence of any additional infections such as cytomegalovirus (CMV) or any non-rejection cause of liver inflammation or injury will need to be accounted for in the control group.

2) Control group (No-ACR): This group comprised eight liver transplant recipients with HCV infection who had similar biochemical profiles as the ACR group, but who did not have cholangitis or endotheliitis histologically. Recipients in the control group did not receive treatment for ACR at any point.

Clinical characteristics of Subjects. The clinical characteristics of both groups are summarized in Table 3. Subjects in the ACR and control groups had similar mean histology activity indices (HAI) and biochemical profiles. Body mass index (BMI, weight in kg/height in $m^2$) and immunosuppression dosing and trough levels were also similar between the groups.

TABLE 3

|  | ACR | No-ACR |
| --- | --- | --- |
| Age | 44.0 +/− 1.5 | 47.8 +/− 2.8 |
| Male/female | 4/4 | 4/4 |
| Total bilirubin | 6.3 +/− 1.9 | 4.2 +/− 1.2 |
| alkaline phosphatase | 771 +/− 150 | 328 +/− 56 |
| AST | 181 +/− 58 | 183 +/− 118 |
| ALT | 316 +/− 66 | 260 +/− 74 |

ACR = acute cellular rejection group,
No-ACR = no acute cellular rejection group.
AST = aspartate transaminase,
ALT = alanine transaminases.
None of the differences were statistically significant.

Immunosuppression. All subjects were treated for immunosuppression with tacrolimus 0.05 mg/kg twice daily (titrated to achieve a target 12 hour trough of 10-15 ng/dl), mycophenolate mofetil 1 g twice daily, and a standard tapering course of corticosteroids.

Serum Samples Studied. Sera from eight subjects from the ACR group and eight subjects from the Control group were obtained in a prospective fashion on day seven post-LT (Table 3). Both the ACR and control groups were matched for age and gender. All subjects in the ACR group who developed classical ACR within twenty-one days post-transplantation demonstrated complete resolution of ACR histologically and biochemically with a single course of methyl prednisolone therapy (1,000 mg on alternate days for a total of 3,000 mg).

Subjects in the control group did not require treatment for ACR at any time and had subsequent allograft histology demonstrating persistent and progressive histological changes consistent with recurrence of HCV infection.

Ten mL whole blood samples were collected in glass tubes without additive (10 mL BD Vacutainer™, Franklin Lakes, N.J.) and allowed to clot at room temperature for forty min. Serum was separated by centrifugation at 1500 rpm for 15 min. One mL aliquots of serum were taken and stored at −80 C until ready for use. The time from collection to frozen storage was no more than thirty min. Samples were collected blind to the investigators participating in the study and contained no identifying features that would make it possible to identify the subjects. The study was approved by the Institutional Review Board of the Mayo Foundation.

Depletion of Serum high abundant proteins. Serum samples were processed using a 4.6×50 mm Multiple Affinity Removal Column (Agilent Technologies, Palo Alto, Calif.), which selectively removes albumin, IgG, IgA, anti-trypsin, transferrin, and haptoglobin from the serum sample, attached to an EZChrome Elite HPLC (Hitachi High Technologies America, San Jose, Calif.). This column can process 100 µL of human serum per sample run. Samples were processed according to manufacturer's instructions. For each sample, a low abundance fraction was collected and buffer exchanged into 10 mM Tris-HCl pH 7.4 using 5000 Da molecular weight cutoff spin concentrators (Agilent Technologies, Palo Alto, Calif.). Protein quantification was performed using Coomassie protein assay reagent (Pierce Biotechnology, Rockford, Ill.), absorbance at 595 nm, with a Bradford protein assay using bovine serum albumin as a protein standard. Approximately 94% of total serum protein is removed by this method.

Protein quantification was performed using the Micro BCA™ Protein Assay kit (Pierce Biotechnology, Rockford, Ill.), absorbance at 562 nm. This kit utilizes bicinchoninc acid (BCA) as the detection reagent, with bovine serum albumin as the protein standard.

Serum protein labeling. 100 µg of proteins from each depleted sample were labeled with iTRAQ according to Applied Biosystems iTRAQ protein labeling protocol (Applied Biosystems, Foster City, Calif.). The proteins were reduced, alkylated, cysteine blocked and digested with trypsin overnight. The tryptic digested peptides of each sample was labeled with either 114, 115, 116 or 117 iTRAQ reagents. The labeled peptides from four different samples; two ACR and two control (matched for age and gender) were mixed together. The combined sample was cleaned up of excess trypsin as well as iTRAQ reagents using Waters c18 Sep-Pak (Milford, Mass.) before mass spectrometric analysis.

Sample preparation for Multidimensional Liquid Chromatography—Tandem mass Spectrometry (LC-MS/MS) analysis. The cleaned up iTRAQ labeled sample was fractionated into 10 fractions on a strong cation exchange column, Biox SCX 300 µm×5 cm (Dionex, Sunnyvale, Calif.) using an off-line Agilent 1100 series capillary liquid chromatography system (Wilmington, Del.). LC/MS/MS analysis of the peptides in each fraction was performed on an Applied Biosystems API Qstar XL quadrupole time of flight mass spectrometer configured with a Protana nano spray ion source (Proxeon, Denmark) and with an Ultimate nano liquid chromatography system (Dionex, Sunnyvale, Calif.). The peptides were separated on a Zorbax C18 100 □m×150 mm microbore column (Agilent, Wilmington, Del.) with a gradient from 5% to 60% buffer B over 120 minutes, where buffer A is 0.1% formic acid/98% water/2% acetonitrile and buffer B is 0.1% formic acid/2% water/98% acetonitrile.

The ms/ms data was obtained via information-dependent acquisition (IDA) mode in the Analyst QS software. This consists of a 1.5 second survey scan from 350-1600 m/z and switching to 2.0 second fragmentation scans on three most intense ions from the survey. These ions were then excluded from repeating for 45 seconds. Collision energy applied was varied automatically depending on the precursor m/z and charge state.

Protein Identification, Quantification and Data Analysis. Protein identification was performed by searching MS/MS spectra against the CDS fasta database (Applied Biosystems, Framingham, Mass.) and quantified using ProQuant software (Applied Biosystems, Framingham, Mass.). The data was further analyzed by ProGroup (Applied Biosystems, Framingham, Mass.), a functionality which provides an important second stage of protein identification analysis. The results of the quantification were normalized using the overall ratio obtained for all tagged peptide pairs in the sample.[12] A difference of 2 SDs, i.e., about a 1.2-fold difference in abundance, was considered to be significant, with a confidence limit of >90% using a simple Gaussian approximation.[12, 13] This approximation would, therefore, apply to normalized expression levels >1.2 or, in reciprocal form, <0.8.

Example 1

Preventing ACR by Monitoring Immunosuppression

A subject who received a solid organ (e.g. heart, liver or kidney) allograft (transplant) four weeks ago is usually maintained on a cocktail of immunosuppressive agents. The immunosuppressive agents might include a calcineurin inhibitor, a corticosteroid and an antiproliferative agent. The purpose of prescribing these agents is to prevent allograft injury through rejection.

All immunosuppressive agents have important side effects and toxicities. Thus, a careful balance between effective dosing and toxicity must be struck for each subject receiving immunosuppressive therapy. Currently, physicians are guided by either drug levels (e.g. for tacrolimus or mycophenolate mofetil) or simple dosing schedules (e.g. for corticosteroids). Knowing the state of immunological activation, as indicated by the differential abundance of one or more of the proteins associated with acute cellular rejection, enables a physician to adjust dosing of immunosuppression until the serum protein profile is not suggestive of incipient acute cellular rejection.

Using a multiplex ELISA method, one, several or all of the proteins described herein could be quantified in the course of a working day from a single serum sample in about the same amount of time required for drug level measurement. As demonstrated herein, subjects with "adequate" (within published target ranges) drug levels can still develop ACR. Therefore, measuring serum proteins associated with ACR enables the physician to adjust drug doses to normalize the serum protein profile and prevent the subject from developing ACR.

For example, a subject with a tacrolimus level of 10 ng/dl but increased abundance of heat shock protein 60, as compared to a standardized upper limit of normal for subjects who do not develop ACR, might have the dosing of tacrolimus increased or a new immunosuppressive agent added to the regimen. Conversely, a subject with a tacrolimus level of 10 ng/dl but who has decreased abundance of heat shock protein 6, when compared to a standardized upper limit of normal for subjects who do not develop ACR, might have the dosing of tacrolimus sequentially lowered to minimize tacrolimus exposure, thus reducing cumulative side-effects/toxicity. Measuring the serum proteins differentially associated with ACR can be used in this fashion to avoid the development of ACR and to minimize side effects of immunosuppressive therapy.

Example 2

Monitoring Immune Activation

Because ACR can cause allograft injury that is indistinguishable from other causes of allograft injury, such as infection or loss of blood supply, measuring serum proteins differentially associated with ACR provides important diagnostic information. For example, a liver transplant recipient might present two months post transplantation with elevated bilirubin and aninotransferase levels. The subject is known to have hepatitis C (HCV) infection. Biopsy findings associated with HCV and ACR can overlap substantially. Levels of ubiquitin conjugating enzyme E2 and beta-2-glycoprotein 1 precursor, measured by multiplex enzyme-linked immunosorbance assay (ELISA) are found to be compatible with ACR when compared to a standardized upper limit of normal for subjects who do not develop ACR. With this knowledge, treatment might focus on increasing immunosuppression for this subject, thereby preventing the subject from developing ACR. Treating HCV in this setting might exacerbate the allograft injury.

Example 3

Diagnosing Acute or Incipient Acute Cellular Rejection

ACR occurs with varying frequencies depending on the organ transplanted. The frequency also varies with host factors, such as age, nutritional status and cause of transplanted organ failure. The development of ACR can adversely affect any transplanted organ, with consequences that can include death or graft loss.

Currently, diagnosing ACR is based on a composite of clinical picture (e.g. rising creatinine for kidney transplant recipients, or rising liver biochemistries for liver transplant recipients) and histology. Histological examination of an allograft necessitates biopsy of the affected organ. Biopsies are expensive, invasive and potentially dangerous procedures. In contrast, measuring serum proteins according to the present invention that are specifically differentially associated with ACR could negate the need for organ biopsies to diagnose rejection (or to determine response to anti-rejection treatment).

For example, a kidney transplant recipient who is six days post transplantation might present with a serial increase in serum creatinine levels. Tacrolimus trough levels are found to be within the target therapeutic range (e.g. 12 ng/dl). Serum levels of ubiquitin conjugating enzyme E2, heat shock protein 60, nuclear factor of activated T-cells (NFAT-1), ubiquitin and heat shock protein 70 are measured and are found to be compatible with ACR when compared to a standardized upper limit of normal for subjects who do not develop ACR. Such a subject can be treated with methylprednisolone pulses to treat ACR without performing a kidney biopsy as the biopsy findings would have demonstrated ACR or incipient ACR.

Example 4

Detecting Change in C3 Using Western Blot

In an example of how detecting a change in a single protein can indicate that a subject having received an organ transplant has or is developing ACR, the amount of complement C3 was detected in biological samples from subjects having ACR via Western Blot analysis and compared to a control. As seen in FIG. 1, an increase in the amount of C3 as compared to the control indicates that the subject has ACR.

Serum was aliquoted from the same samples used for the proteomics analysis to determine whether C3 levels were differentially abundant using an alternative, confirmatory method. Diluted serum samples were subjected to SDS-PAGE under reduced and denaturing conditions and serum proteins transferred to PVDF membranes. The membranes were probed with a commercially available mouse monoclonal antibody against human C3 (1:5000 dilution; Pierce, Rockford, Ill.) that was biotinylated (Molecular Probes Inc., Eugene, Oreg.). Specific binding was detected using horse radish labeled streptavidin (1:10,000; KPL, Gaithersburg, Md.) and an enhanced chemiluminescence system (Pierce, Rockford, Ill.). C3 was seen to be more abundant in the serum of patients with ACR (FIGURE).

Example 5

Single Proteins

Comparing the amount of the single proteins listed in Table 4 in a subject's serum sample to the amounts in a control sample may be used to determine ACR/Immune Activation/Efficacy of Immunosuppression. The proteins described in Examples 5-15 represent a series of specifically envisioned combinations of proteins, wherein a change in protein expression as compared to that of a control may indicate the subject has or is developing ACR. However, other combinations of proteins from Tables 1 and/or 2 are of course also envisioned.

TABLE 4

| | |
|---|---|
| Single protein-A | Ubiquitin conjugating enzyme E2 |
| Single protein-B | Heat shock protein 60 |
| Single protein-C | Nuclear factor of activated T-cells (NFAT-1) |
| Single protein-D | Insulin-like growth factor binding protein |
| Single protein-E | C1-inhibitor precursor |
| Single protein-F | Ribonucleoprotein autoantigen 60 |
| Single protein-G | Beta-2-glycoprotein 1 precursor |
| Single protein-H | Complement C1 Q |
| Single protein-I | Nuclear factor of activated T-cells (NFAT-2) |
| Single protein-J | Heat shock protein 70 |
| Single protein-K | Zinc finger protein 135 |
| Single protein-L | FK506 binding protein 10 precursor |
| Single protein-M | Complement C3 |
| Single protein-N | Heat shock protein C078 |
| Single protein-O | Serum amyloid A1 |
| Single protein-P | Ubiquitin |
| Single protein-Q | Retinol binding protein |

Example 6

Two Protein Panels

Comparing the amount of the following two-protein sets in a subject's serum sample to the amounts in a control sample may be used to determine if the subject has or is developing ACR/immune Activation/Efficacy of Immunosuppression.

TABLE 5

| | |
|---|---|
| Two protein-A | Heat shock protein 60 |
| | Ribonucleoprotein autoantigen 60 |
| Two protein-B | Ubiquitin conjugating enzyme E2 |
| | Ribonucleoprotein autoantigen 60 |
| Two protein-C | Ubiquitin conjugating enzyme E2 |
| | Heat shock protein 60 |
| Two protein-D | Heat shock protein 60 |
| | Insulin-like growth factor binding protein |
| Two protein-E | Heat shock protein 60 |
| | C1-inhibitor precursor |
| Two protein-F | Ubiquitin conjugating enzyme E2 |
| | Insulin-like growth factor binding protein |
| Two protein-G | Ubiquitin conjugating enzyme E2 |
| | C1-inhibitor precursor |
| Two protein-H | Heat shock protein 60 |
| | Beta-2-glycoprotein 1 precursor |
| Two protein-I | Ubiquitin conjugating enzyme E2 |
| | Beta-2-glycoprotein 1 precursor |
| Two protein-J | Nuclear factor of activated T-cells (NFAT-1) |
| | C1-inhibitor precursor |
| Two protein-K | Heat shock protein 60 |
| | Retinol binding protein |
| Two protein-L | Ubiquitin conjugating enzyme E2 |
| | Nuclear factor of activated T-cells |
| Two protein-M | Heat shock protein 60 |
| | Zinc finger protein 135 |
| Two protein-N | Ubiquitin conjugating enzyme E2 |
| | Zinc finger protein 135 |
| Two protein-O | FK506 binding protein 10 precursor |
| | Heat shock protein 60 |
| Two protein-P | FK506 binding protein 10 precursor |
| | Ubiquitin conjugating enzyme E2 |
| Two protein-Q | FK506 binding protein 10 precursor |
| | Nuclear factor of activated T-cells (NFAT-1) |

Example 7

Three Protein Panels

Comparing the amount of the following three-protein sets in a subject's serum sample to the amounts in a control sample may be used to determine if the subject has or is developing ACRI/immune Activation/Efficacy of Immunosuppression.

TABLE 6

| | |
|---|---|
| Three protein-A | Heat shock protein 60, Ribonucleoprotein autoantigen 60 |
| | Ubiquitin conjugating enzyme E2 |
| Three protein-B | Ubiquitin conjugating enzyme E2 |
| | Ribonucleoprotein autoantigen 60 |
| | Heat shock protein 70 |
| Three protein-C | Ubiquitin conjugating enzyme E2, Heat shock protein 60 |
| | Serum amyloid A1 |
| Three protein-D | Heat shock protein 60 |
| | Insulin-like growth factor binding protein |
| | Ubiquitin |
| Three protein-E | Heat shock protein 60, C1-inhibitor precursor |
| | Ubiquitin |
| Three protein-F | Ubiquitin conjugating enzyme E2 |
| | Insulin-like growth factor binding protein |
| | NFAT-1 |
| Three protein-G | Ubiquitin conjugating enzyme E2 |
| | C1-inhibitor precursor |
| | Retinol binding protein |
| Three protein-H | Heat shock protein 60 |
| | NFAT-1 |
| | Beta-2-glycoprotein 1 precursor |
| Three protein-I | Ubiquitin conjugating enzyme E2 |
| | Beta-2-glycoprotein 1 precursor |
| | Complement C3 |
| Three protein-J | Nuclear factor of activated T-cells (NFAT-1) |
| | C1-inhibitor precursor |
| | Beta-2-glycoprotein 1 precursor |

TABLE 6-continued

| | |
|---|---|
| Three protein-K | Heat shock protein 60 |
| | Heat shock protein 70 |
| | Complement C3 |
| Three protein-L | Ubiquitin conjugating enzyme E2 |
| | Complement C3 |
| | C1-inhibitor precursor |
| Three protein-M | Heat shock protein 60 |
| | Zinc finger protein 135 |
| | FK506 binding protein 10 precursor |
| Three protein-N | Ubiquitin conjugating enzyme E2 |
| | Zinc finger protein 135 |
| | FK506 binding protein 10 precursor |
| Three protein-O | FK506 binding protein 10 precursor |
| | Heat shock protein 60 |
| | Insulin-like growth factor binding protein |
| Three protein-P | FK506 binding protein 10 precursor |
| | Ubiquitin conjugating enzyme E2 |
| | Beta-2-glycoprotein 1 precursor |
| Three protein-Q | Ubiquitin conjugating enzyme E2, Heat shock protein 60 |
| | Nuclear factor of activated T-cells (NFAT-1) |

Example 8

Four Protein Panels

Comparing the amount of the following four-protein sets in a subject's serum sample to the amounts in a control sample may be used to determine if the subject has or is developing ACR/Immune Activation/Efficacy of Immunosuppression.

TABLE 7

| | |
|---|---|
| Four protein-A | Ubiquitin conjugating enzyme E2 |
| | Heat shock protein 60 |
| | Nuclear factor of activated T-cells (NFAT-1) |
| | Ribonucleoprotein autoantigen 60 |
| Four protein-B | Ubiquitin conjugating enzyme E2 |
| | Heat shock protein 70 |
| | Retinol binding protein |
| | Ribonucleoprotein autoantigen 60 |
| Four protein-C | Ubiquitin conjugating enzyme E2 |
| | Heat shock protein 60 |
| | Complement C3 |
| | Ribonucleoprotein autoantigen 60 |
| Four protein-D | Ubiquitin conjugating enzyme E2 |
| | Heat shock protein 60 |
| | Complement C3 |
| | C1-inhibitor precursor |
| Four protein-E | Ubiquitin conjugating enzyme E2 |
| | Heat shock protein 60 |
| | Complement C3 |
| | FK506 binding protein 10 precursor |
| Four protein-F | Ubiquitin conjugating enzyme E2 |
| | Heat shock protein 60 |
| | Complement C3 |
| | Insulin-like growth factor binding protein |
| Four protein-G | Ubiquitin conjugating enzyme E2 |
| | Heat shock protein 70 |
| | Complement C3 |
| | C1-inhibitor precursor |
| Four protein-H | Ubiquitin conjugating enzyme E2 |
| | Heat shock protein 60 |
| | Complement C3 |
| | Insulin-like growth factor binding protein |
| Four protein-I | Ubiquitin conjugating enzyme E2 |
| | Heat shock protein 60 |
| | Beta-2-glycoprotein 1 precursor |
| | Insulin-like growth factor binding protein |
| Four protein-J | Ubiquitin conjugating enzyme E2 |
| | Heat shock protein 60 |
| | Complement C3 |
| | Beta-2-glycoprotein 1 precursor |

TABLE 7-continued

| | |
|---|---|
| Four protein-K | Ubiquitin conjugating enzyme E2 |
| | Heat shock protein 60 |
| | Beta-2-glycoprotein 1 precursor |
| | Insulin-like growth factor binding protein |

Example 9

Six Protein Panels

Comparing the amount of the following six-protein sets in a subject's serum sample to the amounts in a control sample may be used to determine if the subject has or is developing ACR/Immune Activation/Efficacy of Immunosuppression.

TABLE 8

| | |
|---|---|
| Six protein-A | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| Six protein-B | Ubiquitin conjugating enzyme E2 |
| | Heat shock protein 60 |
| | Nuclear factor of activated T-cells (NFAT-1) |
| | Ubiquitin |
| | Heat shock protein 70 |
| | Ribonucleoprotein autoantigen 60 |
| Six protein-C | Ubiquitin conjugating enzyme E2 |
| | Heat shock protein 60 |
| | Nuclear factor of activated T-cells (NFAT-1) |
| | Ubiquitin |
| | Heat shock protein 70 |
| | Complement C3 |
| Six protein-D | Ubiquitin conjugating enzyme E2 |
| | Heat shock protein 60 |
| | Nuclear factor of activated T-cells (NFAT-1) |
| | Ubiquitin |
| | Insulin-like growth factor binding protein |
| | Ribonucleoprotein autoantigen 60 |
| Six protein-E | Ubiquitin conjugating enzyme E2 |
| | Heat shock protein 60 |
| | Nuclear factor of activated T-cells (NFAT-1) |
| | C1 inhibitor precursor |
| | Insulin-like growth factor binding protein |
| | Ribonucleoprotein autoantigen 60 |
| Six protein-F | Ubiquitin conjugating enzyme E2 |
| | Heat shock protein 60 |
| | Complement C3 |
| | Ubiquitin |
| | Insulin-like growth factor binding protein |
| | Ribonucleoprotein autoantigen 60 |

Example 10

Eight Protein Panels

Comparing the amount of the following eight-protein sets in a subject's serum sample to the amounts in a control sample may be used to determine if the subject has or is developing ACR/Immune Activation/Efficacy of Immunosuppression.

TABLE 9

| | |
|---|---|
| Eight protein-A | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |

TABLE 9-continued

| | |
|---|---|
| | Insulin-like growth factor binding protein |
| | Ribonucleoprotein autoantigen 60 |
| Eight protein-B | Ubiquitin conjugating enzyme E2 |
| | Heat shock protein 60 |
| | Nuclear factor of activated T-cells (NFAT-1) |
| | Ubiquitin |
| | Heat shock protein 70 |
| | C1 inhibitor precursor |
| | Ribonucleoprotein autoantigen 60 |
| | Insulin-like growth factor binding protein |
| Eight protein-C | Ubiquitin conjugating enzyme E2 |
| | Heat shock protein 60 |
| | Nuclear factor of activated T-cells (NFAT-1) |
| | Ubiquitin |
| | Beta-2-glycoprotein 1 precursor |
| | C1 inhibitor precursor |
| | Ribonucleoprotein autoantigen 60 |
| | Insulin-like growth factor binding protein |
| Eight protein-D | Ubiquitin conjugating enzyme E2 |
| | Heat shock protein 60 |
| | Nuclear factor of activated T-cells (NFAT-1) |
| | Ubiquitin |
| | Heat shock protein 70 |
| | Complement C3 |
| | FK506 binding protein 10 precursor |
| | Insulin-like growth factor binding protein |
| Eight protein-E | Ubiquitin conjugating enzyme E2 |
| | Heat shock protein 60 |
| | Nuclear factor of activated T-cells (NFAT-1) |
| | Ubiquitin |
| | Heat shock protein 70 |
| | C1 inhibitor precursor |
| | NFAT-2 |
| | Insulin-like growth factor binding protein |
| Eight protein-F | Ubiquitin conjugating enzyme E2 |
| | Heat shock protein 60 |
| | Nuclear factor of activated T-cells (NFAT-1) |
| | Ubiquitin |
| | Zinc finger protein 135 |
| | C1 inhibitor precursor |
| | Complement C3 |
| | Insulin-like growth factor binding protein |

Example 11

Ten Protein Panels

Comparing the amount of the following ten-protein sets in a subject's serum sample to the amounts in a control sample may be used to determine if the subject has or is developing ACR/immune Activation/Efficacy of Immunosuppression.

TABLE 10

| | |
|---|---|
| Ten protein-A | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Insulin-like growth factor binding protein |
| | Ribonucleoprotein autoantigen 60 |
| | Beta-2-glycoprotein 1 precursor |
| | C1 inhibitor precursor |
| Ten protein-B | Ubiquitin conjugating enzyme E2 |
| | Heat shock protein 60 |
| | Nuclear factor of activated T-cells (NFAT-1) |
| | Ubiquitin |
| | Heat shock protein 70 |
| | Complement component C1Q |
| | Insulin-like growth factor binding protein |
| | Ribonucleoprotein autoantigen 60 |
| | Beta-2-glycoprotein 1 precursor |
| | C1 inhibitor precursor |

TABLE 10-continued

| | |
|---|---|
| Ten protein-C | Ubiquitin conjugating enzyme E2 |
| | Heat shock protein 60 |
| | FK506 binding protein 10 precursor |
| | Ubiquitin |
| | Heat shock protein 70 |
| | Complement component C1Q |
| | Insulin-like growth factor binding protein |
| | Ribonucleoprotein autoantigen 60 |
| | Beta-2-glycoprotein 1 precursor |
| | C1 inhibitor precursor |
| Ten protein-D | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Insulin-like growth factor binding protein |
| | Ribonucleoprotein autoantigen 60 |
| | FK506 binding protein 10 precursor |
| | C1 inhibitor precursor |

Example 12

Twelve Protein Panels

Comparing the amount of the following twelve-protein sets in a subject's serum sample to the amounts in a control sample may be used to determine if the subject has or is developing ACR/Immune Activation/Efficacy of Immunosuppression.

TABLE 11

| | |
|---|---|
| Twelve protein-A | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | FK506 binding protein 10 precursor |
| | Complement C3 |
| | Heat shock protein C078 |
| | Insulin-like growth factor binding protein |
| | Ribonucleoprotein autoantigen 60 |
| Twelve protein-B | Ubiquitin conjugating enzyme E2 |
| | Heat shock protein 60 |
| | Nuclear factor of activated T-cells (NFAT-1) |
| | Ubiquitin |
| | Heat shock protein 70 |
| | Complement component C1Q |
| | FK506 binding protein 10 precursor |
| | Complement C3 |
| | Beta-2-glycoprotein 1 precursor |
| | C1 inhibitor precursor |
| | Insulin-like growth factor binding protein |
| | Ribonucleoprotein autoantigen 60 |
| Twelve protein-C | Ubiquitin conjugating enzyme E2 |
| | Heat shock protein 60 |
| | Nuclear factor of activated T-cells (NFAT-1) |
| | Ubiquitin |
| | Heat shock protein 70 |
| | Complement component C1Q |
| | FK506 binding protein 10 precursor |
| | Adenylate kinase 7 |
| | Beta-2-glycoprotein 1 precursor |
| | C1 inhibitor precursor |
| | Insulin-like growth factor binding protein |
| | Ribonucleoprotein autoantigen 60 |
| Twelve protein-D | Ubiquitin conjugating enzyme E2 |
| | Heat shock protein 60 |
| | Nuclear factor of activated T-cells (NFAT-1) |
| | Ubiquitin |
| | Heat shock protein 70 |
| | Complement component C1Q |

TABLE 11-continued

| | |
|---|---|
| | Apolipoprotein D |
| | Adenylate kinase 7 |
| | Beta-2-glycoprotein 1 precursor |
| | C1 inhibitor precursor |
| | Insulin-like growth factor binding protein |
| | Ribonucleoprotein autoantigen 60 |

Example 13

Fifteen Protein Panels

Comparing the amount of the following fifteen-protein sets in a subject's serum sample to the amounts in a control sample may be used to determine if the subject has or is developing ACR/Immune Activation/Efficacy of Immunosuppression.

TABLE 12

| | |
|---|---|
| Fifteen protein-A | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | Complement C3 |
| | Complement 4A |
| | Complement 4B |
| | Insulin-like growth factor binding protein |
| | Ribonucleoprotein autoantigen 60 |
| Fifteen protein-B | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | Complement C3 |
| | Complement 4A |
| | Beta-2-glycoprotein 1 precursor |
| | Insulin-like growth factor binding protein |
| | Ribonucleoprotein autoantigen 60 |
| Fifteen protein-C | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | Complement C3 |
| | C1 inhibitor precursor |
| | Beta-2-glycoprotein 1 precursor |
| | Insulin-like growth factor binding protein |
| | Ribonucleoprotein autoantigen 60 |
| Fifteen protein-D | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | C1 inhibitor precursor |
| | Beta-2-glycoprotein 1 precursor |

TABLE 12-continued

Insulin-like growth factor binding protein
Ribonucleoprotein autoantigen 60
Adenylate kinase 7

Example 14

Twenty Protein Panels

Comparing the amount of the following twenty-protein sets in a subject's serum sample to the amounts in a control sample may be used to determine if the subject has or is developing ACR/Immune Activation/Efficacy of Immunosuppression.

TABLE 13

| Twenty protein-A | Ubiquitin conjugating enzyme E2 |
| --- | --- |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | Complement C3 |
| | Complement 4A |
| | Complement 4B |
| | Serine protease inhibitor |
| | Apolipoprotein D |
| | Adenylate kinase 7 |
| | C1 inhibitor precursor |
| | Beta-2-glycoprotein 1 precursor |
| | Insulin-like growth factor binding protein |
| | Ribonucleoprotein autoantigen 60 |
| Twenty protein-B | Ubiquitin conjugating enzyme E2 |
| | Heat shock protein 60 |
| | Nuclear factor of activated T-cells (NFAT-1) |
| | Ubiquitin |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | Complement C3 |
| | Complement 4A |
| | Complement 4B |
| | Serine protease inhibitor |
| | Apolipoprotein D |
| | Alpha fibrinogen precursor |
| | C1 inhibitor precursor |
| | Beta-2-glycoprotein 1 precursor |
| | Insulin-like growth factor binding protein |
| | Ribonucleoprotein autoantigen 60 |

Example 15

Thirty Protein Panels

Comparing the amount of the following thirty-protein sets in a subject's serum sample to the amounts in a control sample may be used to determine if the subject has or is developing ACR/Immune Activation/Efficacy of Immunosuppression.

TABLE 14

| Thirty protein-A | Ubiquitin conjugating enzyme E2 |
| --- | --- |
| | Heat shock protein 60 |
| | Nuclear factor of activated T-cells (NFAT-1) |

TABLE 14-continued

| | Ubiquitin |
| --- | --- |
| | Heat shock protein 70 |
| | Zinc finger protein 135 |
| | Complement component C1Q |
| | Nuclear factor of activated T-cells (NFAT-2) |
| | FK506 binding protein 10 precursor |
| | Heat shock protein C078 |
| | Complement C3 |
| | Complement 4A |
| | Complement 4B |
| | Amyloid A1 |
| | Glyceraldehydes 3-phosphate dehydrogenase |
| | Retinol binding protein |
| | CD33 precursor |
| | FK binding protein 10 |
| | UDP-glucose pyrophosphorylase 2 |
| | Alpha fibrinogen precursor |
| | Serine protease inhibitor |
| | Apolipoprotein D |
| | Apolipoprotein H |
| | Apolipoprotein B-100 |
| | Apolipoprotein C-1 |
| | Adenylate kinase 7 |
| | C1 inhibitor precursor |
| | Beta-2-glycoprotein 1 precursor |
| | Insulin-like growth factor binding protein |
| | Ribonucleoprotein autoantigen 60 |

The major finding of this study is that ACR in transplant recipients is associated with the differential abundance of a distinct set of proteins that can be measured in the serum proteome before ACR is suspected or apparent clinically. From a total of 2801 identified serum proteins only forty-six were differentially abundant in all subjects with ACR when compared to controls. Because high abundance serum proteins were removed, which are typically proteins whose function depends on their presence in serum, the analysis detected proteins present in serum on a transient basis, (e.g. due to cell destruction, or secreted proteins) such as cytokines, receptor ligands and hormones, that rely on serum for transportation to cells at anatomically remote sites.

There are several important implications of the serum proteomic signature of ACR identified herein. Perhaps most obviously, these results provide direct evidence that serum proteins can be used to diagnose ACR. Additionally, the second implication of this proteomic analysis of serum is that several proteins have been identified that, although known to play a role immune activation, appear to be specifically differentially abundant in subjects with incipient/pre-clinical ACR. Whether manipulating levels of activity of these proteins, ubiquitin or CD33, for example, would have an impact on the development of ACR, is unknown.

Limitations and the need for further studies notwithstanding, these results suggest that ACR is associated with the differential abundance of a distinct set of proteins that can be measured in the serum proteome before ACR is apparent clinically. The identification of a distinct serum proteomic signature for ACR, which includes proteins not previously associated with ACR, raises the possibility of new diagnostic and therapeutic approaches to the management of immunosuppression in transplant recipients.

The serum proteome consists of proteins produced by many sources, including lymphocytes and all the components of the liver (e.g. endothelium, cholangiocytes and hepatocytes). Many serum proteins, particularly those produced by lymphocytes, are present in very low abundances. Proteomic analyses of serum have been limited by poor sensitivity in detecting low-abundance proteins, maintaining sample stability and in data management. Recent advances in protein separation, including depletion of highly abundant proteins,[7] and improvements in detection and identification of peptides and proteins,[8] coupled with high-throughput mass spectrometry[9] have facilitated detailed characterization of complex biological samples, including serum.[10, 11]

The lack of existing literature concerning tissue or serum proteomic analyses in general reflects the difficulty in measuring the abundance of low concentration serum proteins. Therefore, the tandem mass spectrometric approach used herein provided simultaneous analysis of the relative expression of a large number of proteins in a sensitive manner to determine the relative expression of serum proteins during ACR. Identifying differentially expressed proteins associated with allograft rejection may generate novel insights into the pathophysiology of ACR. Furthermore, differential cytokine expression analysis might facilitate adjustments to immunosuppression prior to rejection producing histologically apparent end-organ damage.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Demetris A et al. Hepatology 2000 March 31(3):792-799.
2. Wiesner R H et al. 28 ed. 1998. 638-645.
3. Charlton M, Seaberg E. Liver Transplantation & Surgery 1999 July; 5(4:Suppl 1): 107-114.
4. Berenguer M et al. J. Hepatol. 1998 May; 28(5):756-763.
5. Rosen H R et al. Am. J. Gastroenterol 1997 September; 92(9):1453-1457.
6. Sreekumar R et al. Liver Transplantation 2002 September; 8(9):814-821.
7. Bjorhall K, Miliotis T, Davidsson P. Proteomics 2005 January; 5(1):307-317.
8. Qian W J et al. J. Proteome Res. 2005 January; 4(1):53-62.
9. Washburn M P et al. Nature Biotechnology 2001 March; (3):242-247.
10. Petricoin E F et al. Lancet 359 (9306):572-7, Feb. 16, 2002.
11. Jacobs J M et al. J. Proteome Research 2005 July 4(4): 1073-1085.
12. DeSouza L et al. Proteomics 2005 January 5(1):270-281.
13. DeSouza L et al. J. Proteome Res. 2005 March; 4(2):377-386.
14. O'Riordan E et al. J. Am. Soc. Nephrology 15 (12):3240-8, 2004 December.
15. Clarke W et al. Ann. Surgery 237 (5):660-4; discussion 664-5, 2003 May.
16. Schaub S et al. J. Am. Soc. Nephrology 2004 January; 15(1):219-227.
17. Schaub S et al. Am. J. Transplantation 2005 April; 5(4 Pt 1):729-738.
18. Borozdenkova S et al. J. Proteome Res. 3(2):282-8, 2004 March;-April.
19. Martin S E et al. Analytical Chem. Sep. 15, 2000; 72(18): 4266-4274.
20. Belov M E et al. Analytical Chem. May 15, 2000; 72(10): 2271-2279.
21. Gygi S P et al. Nature Biotechnology 1999 October; 17(10):994-999.
22. Chong P K et al. J. Proteome Res. 2006 May; 5(5):1232-1240.
23. Keshamouni V G et al. J. Proteome Res. 2006 May; 5(5):1143-1154.
24. Simpson M A et al. Clinics in Laboratory Medicine 1991 September; 11(3):733-762.
25. Toyoda M et al. Clin. Transplantation 1995 December; 9(6):472-480.
26. Deng M C et al. Transplantation Nov. 27, 1995; 60(10): 1118-1124.
27. Kimball P M et al. Transplantation Mar. 27, 1996; 61(6): 909-915.
28. Wu C J et al. Transplant Immunology 1994 September; 2(3):199-207.
29. Satoh S et al. Transplantation Sep. 27, 1995; 60(6):558-562.
30. Koelman C A et al. Transplant Immunology 2000 March; 8(1):57-64.
31. Venkatesh N et al. Nat. Acad. Sci. 101 (24):8969-74, Jun. 15, 2004.
32. Murphy L L, Hughes C C. J. Immunology 169 (7):3717-25, Oct. 1, 2002.
33. Granja C et al. Hum. Immunology 65 (2):124-34, 2004 February.
34. Birk O S et al. Nat. Acad. Sci. 96 (9):5159-63 Apr. 27, 1999.
35. Lakkis F G. Nature Medicine 2002 October; 8(10):1043-1044.
36. Pratt J R et al. Nature Medicine 2002 June; 8(6):582-587.
37. Marsh J E et al. Transplantation Oct. 1, 1915; 72(7):1310-1318.
38. Griffin J D et al. Leukemia Research 1984; 8(4):521-534.
39. Andrews R G et al. Blood 1983 July; 62(1): 124-132.
40. Nakamura Y et al. Blood Mar. 1, 1994; 83(5):1442-1443.
41. Thomas R, et al. J. Immunology Dec. 15, 1993; 151(12): 6840-6852.
42. Handgretinger R et al. Immunology Letters 1993 August; 37(2-3):223-228.
43. Davey F R et al. Leukemia 1988 July; 2(7):420-426.
44. Raptis A et al. British J. Haematology 102 (5):1354-8, 1998 September.
45. Wicks S J et al. Oncogene Dec. 5, 2001; 24(54):8080-8084.
46. Tanaka T et al. Immunity 2005 June; 22(6):729-736.
47. Gao M et al. Science Oct. 4, 1908; 306(5694):271-275.
48. Rajendra R et al. J. Biol. Chemistry Aug. 4, 1927; 279 (35):36440-36444.
49. Chen Z Y et al. Cancer Research 65 (22):10394-400, Nov. 15, 2005.
50. Zornig M et al. Oncogene Apr. 18, 1996; 12(8):1789-1801.
51. Gilks C B et al. Mol. & Cell. Biology 1993 March; 13(3):1759-1768.
52. van L et al. Cell May 31, 1991; 65(5):737-752.
53. Schreiber S L. Science Jan. 18, 1991; 251(4991):283-287.
54. Patterson C E et al. Cell Stress & Chaperones 2005; 10(4):285-295.
55. Fang Y et al. Science 294 (5548):1942-5, Nov. 30, 2001.
56. Sarbassov D et al. Current Opinion in Cell Biology 17(6): 596-603, 2005 December.

I claim:

1. A method of diagnosing a human subject having received an organ transplant with acute cellular rejection, the method comprising the steps of:
   a) obtaining a blood, plasma or serum sample from the subject;
   b) detecting an amount of at least one protein indicative of acute cellular rejection in the sample, wherein the at least one protein is selected from the group consisting of complement component 1q; complement component 4A; and complement component 4B; and
   c) comparing the amount of the protein in the sample to a control,
   wherein an increase in the amount of the protein in the sample relative to the control indicates the subject has acute cellular rejection.

* * * * *

UNITED STATES PATENT AND TRADEMARK OFFICE
CERTIFICATE OF CORRECTION

PATENT NO. : 8,003,333 B2
APPLICATION NO. : 12/235292
DATED : August 23, 2011
INVENTOR(S) : Michael R. Charlton It is certified that error appears in the above-identified patent and that said Letters Patent is hereby corrected as shown below:

Column 4, line 37 "15" should be --L15--

Column 5, line 44 "bronchioalveolar" should be --bronchoalveolar--

Column 12, line 9 "tacrolimnus" should be --tacrolimus--

Column 15, line 18 "aninotransferase" should be --aminotransferase--

Signed and Sealed this
Eleventh Day of October, 2011

David J. Kappos
*Director of the United States Patent and Trademark Office*